(12) United States Patent
Armstrong et al.

(10) Patent No.: US 7,790,460 B2
(45) Date of Patent: Sep. 7, 2010

(54) METHOD FOR THE REGENERATION OF COTTON

(75) Inventors: Toni A. Armstrong, St. Louis, MO (US); David L. DeBoer, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 458 days.

(21) Appl. No.: 10/692,762

(22) Filed: Oct. 24, 2003

(65) Prior Publication Data

US 2004/0087030 A1 May 6, 2004

(51) Int. Cl.
*C12N 15/82* (2006.01)
*A01H 5/00* (2006.01)
(52) U.S. Cl. ...................... 435/468; 800/314
(58) Field of Classification Search ................. 435/468; 800/314
See application file for complete search history.

(56) References Cited

U.S. PATENT DOCUMENTS

| | | | |
|---|---|---|---|
| 4,672,035 A | | 6/1987 | Davidonis et al. |
| 5,004,863 A | * | 4/1991 | Umbeck .................... 800/314 |
| 5,159,135 A | | 10/1992 | Umbeck |
| 5,244,802 A | * | 9/1993 | Rangan ....................... 435/427 |
| 5,341,557 A | * | 8/1994 | Perlman ...................... 29/446 |
| 5,834,292 A | * | 11/1998 | Rangan et al. .............. 800/268 |
| 5,846,797 A | * | 12/1998 | Strickland ................... 800/294 |
| 6,200,809 B1 | * | 3/2001 | Klimaszewska et al. ..... 435/422 |

FOREIGN PATENT DOCUMENTS

CA 1309367 * 11/1988

OTHER PUBLICATIONS

Adkins et al. Effect of Ethylene and Culture Environment on Rice Callus Proliferation, 1993, Journal of Experimental Botany, vol. 44, No. 269, pp. 1829-1835.*
Hirimburegama et al. In vitro callus and cell cultures of *Gossypium hirsutum* L. (Cotton). 1994, J. Natn. Sci. Coun. Sri Lanka, 22(4):305-312.*
Smith et al. Defined conditions for the initiation and growth of cotton callus in vitro, I . *Gossypiium arboreum*, 1977, In Vitro, vol. 13, No. 5, pp. 329-334.*
Dodds et al Experiments in Plant Tissue Culture, 1985, 2$^{nd}$ ed. pp. 39-43.*

Chi et al. Effects of AgNO3 and aminoethoxyvinylglycine on in vitro shoot and root organogenesis from seedling explants of recalcitrant Brassica genotypes Plant Cell Reports (1990) 9:195-198.*
Davis et al, In vitro culture of callus tissues and cell suspensions from Okra (*Hibiscus esculentus* L.) and cotton (*Gossypium hirsutum* L), In Vitro, vol. 9, No. 6, 1974, pp. 395-398.*
Firoozabady et al. Transformation of cotton (*Gossypium hirsutum* L.) by *Agrobacterium tumefaciens* and regeneration of transgenic plants. Plant Molecular Biology 10:105-116, 1987.*
Gould et al. Regeneration of *Gossypium hirsutum* and *G. barbadense* from shoot apex tissues for transformation, Plant Cell Reports (1991) 10: 12-16.*
Kumar et al. A genetic approach to in vitro regeneration of non-regenerating cotton (*Gossypium hirsutum* L.) cultivars. Plant Cell Reports (1998) 18:59-63.*
Firoozabady et al. Plant regeneration via somatic embryogenesis in many cultivars of cotton (*Gossypium hirsutum* L.), In Vitro Cell. Dev. Biol. 299:166-173, 1993.*
Lashermes. Improved anther culture method for obtaining direct regeneration in wheat (*Triticum aestivum* L.) J. Genet. & Breed. 46:99-102 (1992).*
Database Biosis 'Online! Biosciences Information Service, Phisadelphia, PA US AN PREV198885009003, 1987 Webb, et al.: "Callus formation by ginko-bilboa embryos on hormone-free media controlled by closures and media components" XP002139544, Abstract.
Database WPI, Section Ch, Week 199536, Derwent Publications Ltd., London, GB; AN 1995-271382, XP002139546, Abstract.
Database Biosis 'Online! Biosciences Information Service, Philadelphia, PA, US AN PREV198580016642, 1985, Rikin, et al., "Rhythmicity in cotton *Gossypium-hirsutum* seedlings ethylene production as affected by sylver ions as related to other rhythmic processes", XP002139545, Abstract.
Rifkin et al., Rhythmicity in cotton *Gossypium-hirsutum* seedlings ethylene production as affected bysylver ions as related to other rhythmic processes, *Planta* 163:227-231 (1985).
Webb et al., Callus formation by ginko-bilboa embryos on hormone-free media controlled by closures and media components, *Phytomorphology* 36:121-128 (1986).

* cited by examiner

*Primary Examiner*—June Hwu
(74) *Attorney, Agent, or Firm*—Thomas P. McBride, Esq.; Sonnenschein Nath & Rosenthal LLP

(57) ABSTRACT

Methods for the regeneration of cotton plants are disclosed. The use of selective light conditions, novel compositions of media, and solid support matrices during stages of development resulted in increased frequencies of embryogenesis, embryo maturation and embryo germination. The improved process resulted in higher production frequencies of transformation of cotton.

18 Claims, No Drawings

METHOD FOR THE REGENERATION OF COTTON

This application claims priority to U.S. provisional application 60/112,770 filed Dec. 18, 1998, incorporated herein in its entirety.

FIELD OF THE INVENTION

The invention relates to methods of regenerating cotton plants. Specifically, methods for improving the efficiency of production of cotton plants are disclosed. More specifically, methods utilizing selective light conditions, novel compositions of media, and solid support matrices to increase the frequency of embryogenesis and embryo germination are disclosed.

BACKGROUND OF THE INVENTION

The expanding field of biotechnology provides the tools for scientists to introduce important traits into a variety of plant species. New technologies promote the production of commercially viable transgenic crops and have a significant economic impact on the agricultural industry. These advancements enable creation of new crop germplasm containing desirable novel traits. Such traits include improvements in the nutritional quality, insect resistance, disease resistance, and yield of many crops. Cotton is the leading fiber crop worldwide and holds significant agronomic influence in a number of markets. Accordingly, much effort is continually directed toward the genetic engineering of this agronomically important crop species.

Genetic engineering of plants is essentially a two-step process: transformation and regeneration. First, plant cells are transformed, thereby introducing a nucleic acid sequence that is typically integrated into the genome of the host cell. Second, a sexually competent plant is regenerated from the transformed cells. This regeneration step comprises an induction and a germination phase. The nonembryogenic cotton tissue is induced, under suitable culture conditions, to form embryogenic cotton calli. The embryogenic cotton calli mature, and embryos may then be germinated to form plants. The transformation and regeneration processes preferably are complementary such that the successfully transformed tissues are capable of developing into competent whole plants.

Several methods are available for introducing DNA sequences into plant cells and are well known in the art. Suitable methods include, but are not limited to, bacterial infection, binary bacterial artificial chromosome vectors, direct delivery of DNA (e.g., via PEG-mediated transformation, desiccation/inhibition-mediated DNA uptake, electropbration, agitation with silicon carbide fibers, and acceleration of DNA-coated particles (reviewed in Potrykus, *Ann. Rev. Plant Physiol. Plant Mol. Biol.*, 42: 205, 1991).

Methods for transforming dicots primarily use *Agrobacterium tumefaciens*. Transgenic plants reported include cotton (U.S. Pat. No. 5,004,863 and U.S. Pat. No. 5,159,135). These patents describe the overall regenerative process comprising transformation and selection of a transformed plant tissue, induction of that tissue to form embryos, and germination of those embryos to form a plant. Various media compositions are reported to promote the process. Embryogenesis reportedly required several months.

U.S. Pat. Nos. 5,244,802, 5,583,036, and 5,695,999 disclose methods for regenerating cotton plants from somatic cells. Modified media compositions were reported to be useful at different stages of the regenerative process. More specifically, transformed plant tissue was grown in media supplemented with glucose until phenolic secretions ceased, whereby the tissue was transferred to a media supplemented with sucrose instead of glucose. Many of the cotton lines tested formed transgenic calli but did not undergo embryogenesis and regenerate into a plant.

U.S. Pat. No. 4,672,035 describes a process of regenerating cotton plants utilizing modifications in media composition. Proembryoids were obtained in 1-6 months. Root initiation and growth were reportedly promoted by lowering the glucose concentration in the media.

There exists a need in the art for improved methods for the transformation and regeneration of cotton plants. Such methods may be useful to promote the engineering of desirable traits into this agronomically important crop.

SUMMARY OF THE INVENTION

The methods disclosed in the present invention provide transformation and regeneration techniques to better meet the production needs of cotton breeders and growers. The invention allows more effective production of transgenic cotton germplasm, as well as improved efficiency in the regeneration of whole cotton plants. More specifically, methods utilizing selective light conditions, novel compositions of media, and solid support matrices to increase the frequency of embryogenesis and embryo germination are disclosed.

In a preferred embodiment, the invention comprises improvements in several stages in the preparation of a transgenic cotton plant. The overall process may be summarized as follows:

Preparation of Cotton Tissue

Cotton seeds are sterilized and germinated in the dark or limited light conditions on an appropriate medium such as Murashige and Skoog (MS) (Mursashige and Skoog, *Physiol. Plant*, 15:473-497, 1962). Once the seeds germinate, the hypocotyl segments are removed from the seedlings and cut into small pieces prior to inoculation.

Inoculation and Callus Formation

The hypocotyl pieces are inoculated with Agrobacterium. After co-culture with the Agrobacterium, the inoculated tissue is transferred to a selective media containing media components to initiate callus formation. The nonembryogenic cotton callus is then transferred to a media to stimulate the formation of embryogenic cotton callus.

Induction of Embryogenic Cotton Callus

The cotton calli are monitored for the formation of embryogenic cotton calli. The induction media used in this culture preferably contains an ethylene inhibitor. The media also preferably contains an antioxidant. The culture is preferably maintained under dark or limited lighting conditions or, alternatively, under green light.

Maturation of Embryogenic Cotton Callus

As embryogenic cotton callus develops, it is transferred to embryo maturation media. Non-embryogenic tissue, on the other hand, is returned to the same induction culture described and monitored for the formation of embryogenic tissue. The maturation media used is preferably supplemented with a mixture of amino acids. The culture also preferably contains a solid support matrix. The transgenic cotton embryos are maintained in this culture until they mature (i.e., grow to a suitable size, typically several millimeters in length). Tissue is cultured under dark or limited light conditions, and each plate is sealed with a suitable sealing material, including, but not limited to, PARAFILM M.

Embryo Germination

Larger cotton embryos of several millimeters in length are preferably transferred to a separate culture containing germination media. The germination media contains a carbohydrate, preferably present in the media at a low concentration. The embryos are cultured on this media until they germinate and develop into small plants, preferably having 3-4 leaves. The small plants are subsequently transferred to a larger size culture containing the same germination media and allowed to develop further. After more leaves develop, typically 4-6 total, the plants are preferably transferred to a suitable soil for further growth and testing.

In general, the invention is suitable for the regeneration of plants from any strain of cotton. The methods disclosed are amenable to any Gossypium species.

The cotton tissue selected for transformation may be any source tissue or plant part capable of producing callus that subsequently regenerates into a cotton plant. The tissue is preferably from a hypocotyl, cotyledon, root, floral tissue, petiole, anther, or leaf. More preferably, the tissue is a hypocotyl.

Transformation of the cotton callus may generally be accomplished using any technique known to those of skill in the art for introducing nucleic acids into cells. The transformation is preferably carried out using bacterial infection, binary bacterial artificial chromosome vectors (BIBAC), direct delivery of nucleic acid (e.g., PEG-mediated transformation), desiccation/inhibition-mediated nucleic acid uptake, electroporation, agitation with silicon carbide fibers, acceleration of particles coated with nucleic acid, or by any other method known to those of skill in the art, more preferably by bacterial infection, even more preferably by Agrobacterium infection, and most preferably by Agrobacterium tumefaciens infection.

In general, any strain of Agrobacterium tumefaciens is suitable for transforming the callus. The Agrobacterium tumefaciens strains used are preferably C58; LBA4404, EHA101, EHA105, or EHA109, and more preferably is strain C58.

After transforming the cells and selecting for the transformants, the transgenic callus tissue may be cultured on induction media of a novel composition to promote the formation of embryogenic callus.

The induction media used for the production of embryogenic cotton callus may contain an ethylene inhibitor. The ethylene inhibitor may generally be any ethylene inhibitor compatible with the described invention. The ethylene inhibitor is preferably acetylsalicylic acid, aminoethoxyvinylglycine (AVG), amino-oxyacetic acid (AOA), 2,4-dinitrophenol, cobalt salts, nickel salts, 2,4-norbornadiene, salicylic acid, silver nitrate, or silver thiosulfate, and most preferably is aminoethoxyvinylglycine (AVG). The optimal concentration of the ethylene inhibitor in the induction media varies with the ethylene inhibitor selected.

The induction media used for the production of embryogenic cotton callus may contain an antioxidant. Any antioxidant is compatible with the described invention. The antioxidant is preferably activated charcoal, ascorbic acid, citric acid, cysteine hydrochloride, dithiothreitol (DTT), glutathione, mercaptoethanol, polyvinylpyrrolidine (PVP), polyvinylpolypyrrolidine (PVPP), sulfites, or vitamin E, and more preferably is ascorbic acid. The sulfite may generally be any sulfite containing salt, and is preferably provided as a monovalent salt such as sodium sulfite or potassium sulfite.

The concentration of the antioxidant in the induction media varies with the antioxidant selected. For ascorbic acid the concentration is preferably between about 2.5 mg/L and about 500 mg/L, more preferably between about 5 mg/L and about 250 mg/L, and most preferably between about 10 mg/L and about 100 mg/L.

Cotton callus is cultured under dark or limited lighting conditions during the induction of embryogenic cotton callus. The dark or limited lighting conditions are preferably between about 0 μEinsteins $m^{-2}sec^{-1}$ and about 5 μEinsteins $m^{-2}sec^{-1}$, more preferably between about 0 μEinsteins $m^{-2}sec^{-1}$ and about 3 μEinsteins $m^{-2}sec^{-1}$, even more preferably between about 0 μEinsteins $m^{-2}sec^{-1}$ and about 1 μEinsteins $m^{-2}sec^{-1}$, and most preferably about 0 μEinsteins $m^{-2}sec^{-1}$ (i.e., total darkness).

After embryogenic callus forms, it is preferably transferred to a culture containing a maturation media. The maturation media used in the preparation of mature cotton embryos preferably contains a solid support matrix. The solid support matrix may generally be any type of solid support compatible with the present invention, more preferably a silica/alumina chip, cloth, felt, paper towel, or filter paper, and most preferably filter paper. The culture plates are wrapped with a suitable sealing material, including, but not limited to, wax film, tape, or plastic wrap. Preferably the sealing material is PARAFILM M laboratory film (American National Can, Chicago, Ill.).

The maturation media used in the preparation of mature cotton embryos is preferably supplemented with a mixture of amino acids. Any composition containing all twenty naturally occurring amino acids is generally suitable for the present invention. Therefore, both naturally occurring and synthetic mixtures of the twenty amino acids are encompassed. The amino acid supplements may be provided as a mixture of each of the individual amino acids derived from individual stock powders or solutions. Alternatively, the mixture of amino acids may be provided as a composition derived from a hydrolysate of proteinaceous matter. Examples of such compositions include casein hydrolysates of bovine, sheep, goat, or human milk; hydrolysates of soy, meat, or lactalbumin; dried yeast extracts; and bacterial peptone.

The concentration of the mixture of amino acids in the media may generally be any concentration compatible with the present invention. The preferred concentration of the amino acid supplements will vary depending on the type of supplement selected for use. For example, in naturally occurring extracts, large variations in composition are possible due to differences in the source of the extract.

In the present invention, the concentration of the amino acid supplement is preferably between about 1 mg/L and about 1000 mg/L, more preferably between about 10 mg/L and about 500 mg/L, even more preferably between about 20 mg/L and about 250 mg/L, and most preferably between about 50 mg/L and about 150 mg/L.

During maturation, the embryos are cultured under dark or limited lighting conditions during the induction of embryogenic cotton callus. The dark or limited lighting conditions are preferably between about 0 μEinsteins $m^{-2}sec^{-1}$ and about 5 μEinsteins $m^{-2}sec^{-1}$, more preferably between about 0 μEinsteins $m^{-2}sec^{-1}$ and about 3 μEinsteins $m^{-2}sec^{-1}$, even more preferably between about 0 μEinsteins $m^{-2}sec^{-1}$ and about 1 μEinsteins $m^{-2}sec^{-1}$, and most preferably about 0 μEinsteins $m^{-2}sec^{-1}$ (i.e., total darkness).

The media used to germinate the mature embryos into plants may contain a carbohydrate. Generally, any carbohydrate is suitable for the present invention. The carbohydrate is preferably glucose, sucrose, fructose, maltose, mannose, or xylose, more preferably is glucose or sucrose, and most preferably is glucose.

The concentration of the carbohydrate will vary, depending on the carbohydrate used. For the carbohydrate glucose used in the present invention, the concentration is preferably between about 0.05% (w/v) and about 1% (w/v) and more preferably between about 0.05% (w/v) and about 0.5% (w/v).

Definitions

The following definitions are provided in order to aid those skilled in the art in understanding the detailed description of the present invention.

"Amino acid supplement" or "amino acid mix" refers to any naturally occurring or synthetically derived composition containing a mixture of amino acids. The term encompasses compositions derived from proteinaceous matter, as well as compositions made by mixing together individual amino acids from their respective stock solutions or powders.

"Callus" refers to an undifferentiated proliferating mass of cells or tissue in vitro.

"Coding sequence" and "open reading frame" refer to a region of continuous sequential nucleic acid triplets encoding a protein, polypeptide, or peptide sequence.

"Dark or limited lighting conditions" refers to visible light having a maximum intensity from about 0 μEinsteins $m^{-2}sec^{-1}$ to about 5 μEinsteins $m^{-2}sec^{-1}$.

"Dicot" or "dicotyledon" refers to plants that produce an embryo with two cotyledons. Examples of dicots include cotton, soybean, and peanut.

"Embryogenic callus" refers to a type a callus capable of differentiating into somatic embryos.

"Endogenous" refers to materials originating from within the organism or cell.

"Exogenous" refers to materials originating from outside of the organism or cell. This typically applies to nucleic acid molecules used in producing transformed or transgenic host cells and plants.

"Green light" refers to visible light having a maximum intensity within the wavelength range of about 480 nm to about 545 nm.

"Hybridization" refers to the ability of a strand of nucleic acid to join with a complementary strand via base pairing. Hybridization occurs when complementary sequences in the two nucleic acid strands bind to one another.

"Monocot" refers to plants having a single cotyledon (the first leaf of the embryo of seed plants). Examples of monocots include cereals such as maize, rice, wheat, oats, and barley.

"Non-embryogenic callus" refers to a type of callus composed of undifferentiated, often highly vacuolated cells that have not yet undergone embryogenesis.

"Nucleic acid" refers to deoxyribonucleic acid (DNA) and ribonucleic acid (RNA).

"Phenotype" refers to traits exhibited by an organism resulting from the interaction of genotype and environment.

"Polyadenylation signal" or "polyA signal" refers to a nucleic acid sequence located 3' to a coding region that promotes the addition of adenylate nucleotides to the 3' end of the mRNA transcribed from the coding region.

"Promoter" or "promoter region" refers to a nucleic acid sequence, usually found upstream (5') to a coding sequence, that controls expression of the coding sequence by controlling production of messenger RNA (mRNA) by providing the recognition site for RNA polymerase or other factors necessary for start of transcription at the correct site.

"Recombinant nucleic acid vector" refers to any agent such as a plasmid, cosmid, virus, autonomously replicating sequence, phage, or linear or circular single-stranded or double-stranded DNA or RNA nucleotide segment, derived from any source, capable of genomic integration or autonomous replication, comprising a nucleic acid molecule in which one or more nucleic acid sequences have been linked in a functionally operative manner. Such recombinant nucleic acid constructs or vectors are capable of introducing a 5' regulatory sequence or promoter region and a DNA sequence for a selected gene product into a cell in such a manner that the DNA sequence is transcribed into a functional mRNA, which is subsequently translated into a polypeptide or protein. Recombinant nucleic acid constructs or recombinant vectors may be constructed to be capable of expressing antisense RNAs, in order to inhibit translation of a specific RNA of interest.

"Regeneration" refers to the process of growing a plant from a plant cell (e.g., plant protoplast or explant).

"Selectable marker" refers to a nucleic acid sequence whose expression confers a phenotype facilitating identification of cells containing the nucleic acid sequence. Selectable markers include those which confer resistance to toxic chemicals (e.g., ampicillin resistance, kanamycin resistance), complement a nutritional deficiency (e.g., uracil, histidine, leucine), or impart a visually distinguishing characteristic (e.g., color changes or fluorescence).

"Transcription" refers to the process of producing an RNA copy from a DNA template.

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

"Transgenic" refers to organisms into which exogenous nucleic acid sequences are integrated.

"Vector" refers to a plasmid, cosmid, bacteriophage, or virus that carries exogenous DNA into a host organism.

"Visible light" refers to light detectable to the human eye. This corresponds to light within the wavelength range of about 400 nm to about 700 nm.

DETAILED DESCRIPTION OF THE INVENTION

The present invention discloses improved methods for the preparation of transgenic plants. It has particular utility with dicot species, especially those that have proven recalcitrant to previous transformation protocols. The preferred embodiment utilizes the disclosed methods to generate transgenic cotton plants. The improvements are accomplished through the utilization of selective light conditions, novel compositions of media, and solid support matrices to increase the frequency of embryogenesis and embryo germination following the transformation.

To initiate a transformation process in accordance with the present invention, it is first necessary to construct a recombinant nucleic acid vector. This molecule is defined above and comprises a promoter, a coding sequence or other nucleic acid sequence of interest (e.g., having agronomic utility), a polyadenylation signal, a 3'-termination sequence, and a coding sequence for a selectable marker.

Means for preparing recombinant vectors are well known in the art.

The present invention utilizes recombinant nucleic acid vectors that are generally functional in cotton and other plant species. A number of promoters that function in plant cells have been described in the literature and are derived from a variety of sources. These plant-specific promoters include the nopaline synthase (NOS) and octopine synthase (OCS) promoters, carried on tumor-inducing plasmids of *Agrobacterium tumefaciens*; the caulimovirus promoters, such as the cauliflower mosaic virus (CaMV) 19S and 35S promoters and the figwort mosaic virus (FMV) 35S promoter; the enhanced CaMV35S promoter (e35S); the light-inducible promoter from the small subunit of ribulose bisphosphate carboxylase (ssRUBISCO, a very abundant plant polypeptide); and promoters from actin and the chlorophyll a/b binding proteins. All of these promoters have been used to create various types of DNA constructs that have functioned successfully in plants (PCT publication WO 84/02913).

Modified promoters can be constructed to provide or alter particular regulatory features. Such activities include enhanced transcriptional activity (U.S. Pat. No. 5,106,739), inducibility, tissue-specificity, and developmental stage-specificity. In plants, promoters that are inducible, of viral or synthetic origin, constitutively active, and temporally regulated and spatially regulated have been described (see, for example, Odell et al., *Nature* 313: 810-812, 1985). Other promoters that function in a similar manner are also known in the art and have utility in the practice of this invention.

The promoters described may be further modified to further affect various regulatory features. Such promoters can be produced through combination with other regulatory elements (e.g., operators and enhancers), random mutation, or site-directed mutagenesis. For example, a promoter may be altered to contain multiple enhancer sequences to assist in elevating gene expression.

The recombinant nucleic acid vector typically comprises the regulatory elements sufficient for transcription of a mRNA. These elements include a 5' promoter sequence, a 5' non-translated sequence, a poly-A signal, and a 3' termination signal. These elements may be derived from a variety of sources. The DNA sequences may be isolated for use from viruses, other eukaryotic cells, or be of synthetic origin.

In addition to the regulatory elements, the recombinant vector may also contain a selectable marker. The nucleic acid sequence serving as the selectable marker functions to produce a phenotype in cells that facilitates their identification relative to cells not containing the marker. Useful selectable markers include β-glucuronidase (GUS), green fluorescent protein (GFP), luciferase (LUX), antibiotic resistance sequences, and herbicide tolerance sequences.

Characteristics of useful selectable markers for plants have been outlined in a report on the use of microorganisms (Advisory Committee on Novel Foods and Processes, July 1994). These characteristics include stringent selection with minimal contaminating nontransformed tissue, high numbers of independent transformation events without interference in subsequent regenerative steps, application to a large number of species, and availability of an assay to detect the marker. Several antibiotic and herbicide resistance markers satisfy these criteria (Dekeyser et al., *Plant Physiol.*, 90:217-223, 1989; Della-Cioppa et al., Bio/Technology, 5:579-584, 1987). Antibiotic resistance to kanamycin (and neomycin, G418, bleomycin) is provided by nptII, hygromycin B by aph IV, and gentamycin by aac3 or aacC4. Resistance to herbicides like glyphosate is also described.

In addition to the other components, the recombinant nucleic acid vector contains a DNA coding sequence of interest. These sequences may comprise any sequence of nucleic acids but are preferably those that code for proteins, polypeptides, or peptides conferring a desired trait, or phenotype. Examples of such traits include pest tolerance, herbicide tolerance, improvements in yield, nutritional enhancement, environmental or stress tolerance, or any other desirable changes in plant growth, development, and morphology.

In cotton, the coding sequence of a *Bacillus thuringiensis* (B.t.) crystal toxin has been successfully used to provide resistance to lepidopteran and coleopteran insects. Cotton has been successfully transformed with a B.t. gene, thereby rendering the plant tolerant to the effects of these pests. Others have used a glyphosate-tolerance coding sequence to rendering the cotton plants tolerant to glyphosate herbicides (Nida et al., *J. Agric. Food Chem.*, 44:1960-1966, 1996). Thus there are a variety of possible traits that may have agronomic significance. Any of these DNA coding sequences may be useful in the practice of the transformation methods disclosed herein.

Alternatively, the DNA coding sequence may be placed in a reverse orientation in the recombinant nucleic acid vector so as to produce an anti-sense RNA molecule. This molecule may be capable of hybridizing with a complimentary sequence in the cell. By hybridizing in this fashion, the anti-sense RNA molecule may completely or partially inhibit the translation of the complementary sequence (Schuch et al., *Symp. Soc. Exp. Biol.* 45:117-127, 1991; Bird et al., *Biotech Gen. Engin. Rev.*, 9:207-227, 1991).

The RNA produced from the DNA coding sequence may also be a catalytic RNA molecule (e.g., a ribozyme). This class of RNA is designed to cleave another specific endogenous mRNA, which may effectively neutralize the normal function of the target RNA (see, for example, Gibson, *Mol. Biotechnol.* 7:125-137, 1997).

Not only may the DNA coding sequences have a variety of biological functions, as described above, they may also originate from diverse sources. The sequences may be derived from the same species of plant, a different species of plant, or a different organism. In addition, the sequence may comprise a synthetic nucleic acid or a naturally occurring sequence that has been manipulated using molecular biological techniques.

In light of this disclosure, there exist numerous sequences from diverse sources with a large variety of functions. The foregoing discussion is provided by way of example and is not intended to be exhaustive. Any sequence of nucleic acid, regardless of source or function may have utility in the present invention.

After the construction of the plant transformation vector or construct, the recombinant nucleic acid vector may be introduced into a suitable host such as *Escherichia coli* and mated into another suitable host such as Agrobacterium, or alternatively, directly transformed into competent Agrobacteria. These techniques are well known to those of skill in the art and have been described for a number of plant systems, including cotton (U.S. Pat. Nos. 5,004,863 and 5,159,135).

Agrobacterium-mediated transfer is a widely applicable system for transforming plants because the DNA sequence can be introduced into whole plant tissues, thereby bypassing the need for using protoplast to regenerate an intact plant. The use of Agrobacterium to introduce DNA sequences into plant cells is well known in the art (Fraley et al., *Proc. Natl. Acad. Sci. U.S.A.*, 80: 4803-4807, 1987; Rogers et al., *Annu. Rev. Plant Physiol.*, 38:467486, 1987). Furthermore, the integration of the T-DNA is a relatively precise process, resulting in few rearrangements. The DNA sequence being transferred is defined by border sequences that enable the intervening DNA sequence to be inserted into the plant genome.

Agrobacterium transformation vectors are capable of replication in *Escherichia coli* as well as Agrobacterium, thereby allowing for convenient manipulations (Klee, et al., *Bio/Technology*, 3:637-642, 1985). Moreover, recent technological advances in the structure of the vectors have simplified the process of inserting a specific DNA coding sequence into the vector in a suitable orientation. The structural improvements of these vectors comprise a convenient multi-cloning region containing multiple restriction sites, a flanking 5' promoter region, and a 3' polyadenylation site. The gene of interest is ligated into the multi-cloning site and is thus operably linked to the necessary 3' and 5' regulatory elements (Rogers et al., *Methods Enzymol.*, 153:253-277, 1987). In addition, Agrobacterium containing both armed and disarmed Ti genes can be used.

There are many variations of these types of vectors, and any that contain the necessary elements for producing mRNA from an inserted DNA coding sequence in a plant cell are suitable for participation in the invention. In those plant strains where Agrobacterium-mediated transformation is efficient, the use of Agrobacterium is preferred due to the facile and defined nature of the gene transfer.

The present invention encompasses the use of bacterial strains to introduce genes into cotton plants. In the preferred embodiment, *Agrobacterium tumefaciens* is utilized for the transformation. Preferred *A. tumefaciens* strains include nopaline strains such as C58; octopine strains like LBA4404; and agropine strains such as EHA105, EHA101, and EHA109.

The transformation is typically performed on a specific type of plant tissue. The present invention is compatible with any regenerable cotton tissues (i.e., tissue capable of forming a differentiated plant). Such tissue includes callus tissue, hypocotyl tissue, cotyledons, roots, floral tissue, petioles, anthers, and leaves. In the practice of the present invention, the regenerable tissue is preferably hypocotyl explants.

Preparation of Agrobacteria for inoculation of explants is generally well known to those of skill in the art. For purposes of the present invention, the Agrobacterium culture is initiated by inoculating a petri plate containing media such as Luria-Burtani (LB) in agar with selective antibiotics. The concentrations of selective agent as well as the particular selective agent utilized is variable and depends on the host strain. Those of skill in the art are also aware that the timing of culture growth, culture temperature, and concentration of host bacterium may be different for particular transformation systems. The inoculated plate is incubated between about 23° C. and about 30° C., and preferably between about 26° C. and about 28° C. for several days. An individually isolated colony is used to inoculate a LB liquid culture containing selective antibiotics and grown to the proper concentration. The fresh liquid culture is subsequently used for inoculation of the hypocotyl explants.

Preparation of hypocotyl explant tissue generated from cotton seeds is well known to those of skill in the art (e.g., U.S. Pat. No. 5,159,135). Briefly, cotton seeds are sterilized and germinated in the dark on appropriate media. In a preferred embodiment, ½ Murashige and Skoog (MS) salts without additives are used. Seeds typically germinate in about three to twelve days, and preferably in about five to eight days. Hypocotyl segments are removed from the seedlings, sectioned into small pieces between about 3 mm and about 10 mm in length, and inoculated with Agrobacterium harboring a recombinant nucleic acid vector. The co-culture is allowed to proceed from one to five days, preferably one to three days at room temperature (i.e., about 22° C.-24° C.). After the co-culture step, the excess Agrobacteria are removed.

The tissue is subsequently transferred to selective media containing one or more antibiotics to prevent the growth of the Agrobacterium. The range of inhibitory antibiotics may vary, depending on the Agrobacterium strain used. Those of skill in the art are familiar with the antibiotics used to inhibit Agrobacterium remaining in the culture while allowing growth of the transgenic explant tissue. Examples of Agrobacterium inhibitory antibiotics useful for practice of this invention include carbenicillin and cefotaxime.

In addition to antibiotics to inhibit the growth of Agrobacteria, a selective agent is added to promote the growth of the transformed plant tissue. The selection agent is a substance that is toxic to non-transformed cotton cells but not to transformed cells. The transformed cells generally incorporate and produce a selectable marker at a level suitable to confer resistance to the selection agent. Selection agents used may generally be any selection agent compatible with the present invention. The selection agent is preferably kanamycin, at a concentration between 15 mg/L and 150 mg/L, or glyphosate, at a concentration between 0.5 mM and 2.5 mM. One skilled in the art will appreciate that the concentration of the selective agent may vary with the culture media employed as well as the particular selective agent utilized.

Many different forms of media are suitable for the selection culture. One skilled in the art is familiar with the varieties of media that, when supplemented appropriately, support plant tissue growth and development. Examples of such media would include, but are not limited to, MS media (Murashige and Skoog, *Physiol. Plant*, 15: 473-497, 1962) Gamborg's media (Gamborg et al., *Exp. Cell Res.*, 50:151, 1968), Woody Plant Media (WPM) (McCown and Lloyd, *Hort. Science* 16:453, 1981), Nitsch and Nitsch media (Nitsch and Nitsch, *Science* 163:85-87, 1969), and Schenk and Hildebrandt media (Schenk and Hildebrandt, *Can. J. Bot.* 50:199-204, 1972). Any of these culture media, as well as any equivalent forms, fall within the scope of the present invention. In a preferred embodiment, the culture media is MS media, wherein the MS media typically contains additives. The additives generally comprise vitamins such as $B_5$, phytohormones such as 2,4-D and kinetin, and a carbohydrate source such as glucose.

Those of skill in the art are aware of other important variables that may be altered in the tissue culture conditions. Temperature is one such variable. The transformation and regeneration processes are generally performed in a temperature range between about 20° C. and about 30° C. Preferred ranges for callus induction, induction of embryogenesis, embryo maturation, and embryo germination are from about 26° C. and about 29° C. Another variable is the amount of light provided to the cultures. Plant tissue is typically cultured with a 16-hour day and 8-hour photoperiod with light intensities between about 20 µE and about 1000 µE, unless other conditions are specified.

The transformed tissue is maintained in the selection media, or an equivalent one, for about two to ten weeks, preferably about four to six weeks. Transfers are performed as needed, generally every three to five weeks.

The callus tissue is removed from the hypocotyl pieces and transferred to a media suitable for the induction of embryogenic callus tissue. As stated above, multiple compositions of media are applicable to the present invention. The media is preferably an MS-based media, which may comprise MS salts, vitamin $B_5$, an antioxidant, an ethylene inhibitor, a carbohydrate source, a selection agent, and a gelling agent such as GELRITE (GELRITE is registered trademark of Monsanto Co., St. Louis, Mo.) or PHYTAGEL (PHYTAGEL is a registered trademark of Sigma Chemical Co., St. Louis, Mo.). The gelling agent is typically added at a concentration between about 2 g/L and about 3 g/L.

The induction media generally contains an antioxidant to promote the process of embryogenesis. A combination of antioxidants was found to decrease tissue necrosis in grape-Agrobacterium interactions (Perl et al., *Nature Biotechnology* 14: 624-628, 1996). Those of skill in the art are familiar with the broad range of antioxidants available. The antioxidant is preferably cysteine hydrochloride, ascorbic acid, citric acid, polyvinylpyrrolidone (PVP), polyvinylpolypyrrolidone (PVPP), activated charcoal, dithiothreitol (DTT), vitamin E, mercaptoethanol, glutathione, or a sulfite salt, and more preferably is ascorbic acid. Any number of antioxidants at a concentration suitable to their biological activity are envisioned to have utility in the practice of the present invention and fall within its scope.

The induction media generally contains an ethylene inhibitor to promote the process of embryogenesis. The ethylene biosynthetic pathway involves several steps and is outlined as follows:

Methionine→S-Adenosylmethionine→Aminocyclopropane-1-Carboxylate (ACC)→Ethylene.

Ethylene is a gaseous phytohormone that has an effect on numerous phases of plant morphogenesis, particularly the growth and development of cultured cells in vitro. For a recent review, see Kumar et al., *In Vitro Cell Dev. Biol.*, 34:94-103, 1998. It has been reported that the pathway leading to the production of ethylene can be inhibited at one or more steps The resulting effects of ethylene inhibition on plant growth and development are varied, depending on the plant system and the inhibitor(s) tested. (Roustan et al., *Plant Cell Reports*, 8: 182-185; Purnhauser et al., *Plant Cell Reports*, 6: 1-4, 1987; De block, *Theor. Appl. Genet.*, 76:767-774, 1988; Chi and Pua, *Plant Science*, 64:243-250, 1989; Meijer and Brown, *J. Exp. Bot.*, 39:263-270, 1988).

Those of skill in the art are familiar with the broad range of ethylene inhibitors available. Any compound that is capable of blocking any of the steps in the ethylene biosynthetic pathway, either directly or indirectly, is compatible with the present invention and falls within its scope. The ethylene inhibitor is preferably aminoethoxyvinylglycine (AVG), amino-oxyacetic acid (AOA), cobalt, nickel, 2,4-dinitrophenol, salicylic acid, acetylsalicylic acid, silver nitrate, silver thiosulfate, and 2,5-norbornadiene, and most preferably is aminoethoxyvinylglycine. The preferred concentration of the ethylene inhibitor will vary but should generally be present at a sufficient concentration to block one of the aforementioned biosynthetic steps.

The culture conditions typically include incubation between about 26° C. and about 29° C. under dark or limited lighting conditions. The dark or limited lighting conditions may be accomplished within a bag. Other functionally equivalent devices may also be used. Such devices may include a dark covering material (e.g., foil) or a dark chamber or container designed to allow gas exchange while restricting light exposure. A filter or other device may also be used to limit the light. A colored filter may be used that allows only a specific color of light to pass through. The filter may also be designed to limit the intensity of any light that passes through it. Alternatively, the filter may be dark and essentially block the light completely. Alternatively, the culture may be maintained under green light. The tissue is incubated under these conditions for a period of about two to about fourteen weeks, and preferably about eight to about ten weeks.

The method of the present invention encompasses the use of culture media containing amino acid mixtures. Any composition containing all twenty naturally occurring amino acids is generally suitable for participation in the present invention. This encompasses both naturally occurring and synthetic mixtures of the twenty amino acids. The amino acids may be provided as a mixture of each of the individual amino acids derived from individual stock powders or solutions. Alternatively, the mixture of amino acids may be provided as a composition derived from proteinaceous matter. Examples of such compositions include casein hydrolysates of bovine, sheep, goat, or human milk; hydrolysates of soy, meat, or lactalbumin; dried yeast extracts; and bacterial peptone. Any composition providing all twenty naturally occurring amino acids would function equivalently and is compatible with the present invention.

From about eight to ten weeks after transfer to the induction media, the transformed callus tissue is visually checked for the production of embryogenic callus. This determination may occasionally require microscopic examination of the tissue. Embryogenic callus is removed from non-embryogenic callus. The non-embryogenic tissue is returned to the induction media under conditions of low light and periodically checked for the formation of embryogenic tissue. The embryogenic tissue is typically cultured on an MS-based media comprising MS salts, vitamin $B_5$, a gelling agent, and an amino acid supplement (e.g., casein hydrolysate). Additionally, the media may contain a solid support matrix. This matrix is typically added on top of the agar. The support matrix may be any material that allows access to the necessary nutrients from the media while providing support for the tissue. The support matrix is preferably filter paper, a paper towel, felt, a silica/alumina chip, or any functionally equivalent material, and more preferably is smooth, tightly woven filter paper.

Once the tissue has become embryogenic, any lighting conditions are acceptable, but the use of dark or limited lighting conditions or green light is preferred. The culture plates are wrapped with a sealing material, preferably PARAFILM M.

In a preferred embodiment, embryogenic callus tissue is transferred to semi-solid nutrient media comprising MS salts, vitamin $B_5$, 0.1% (w/v) casein hydrolysate, 1.9 g/L $KNO_3$, solidified with PHYTAGEL, GELRITE, or a similar gelling agent.

Approximately every six weeks, preferably every two to six weeks, most preferably every three to five weeks, actively growing tissue and small embryos are removed and placed in petri plates containing fresh media with a support matrix as described. The plates are cultured at about 28° C. with an approximate 16/8 hour day/night cycle with light ranging between about 20 μE to about 100 μE.

Embryos larger than about 5 mm are individually transferred to an embryo germination media. This media is preferably Stewart and Hsu (SHSU) media (Stewart and Hsu, *Planta* 137:113-117,1977). The germination media typically contains a carbohydrate. The carbohydrate is preferably glucose or sucrose present at a concentration between about 0.1% (w/v) and about 1.0% (w/v), and more preferably is between about 0.1% (w/v) and about 0.5% (w/v). Other carbohydrates including fructose, maltose, mannose, and xylose are also envisioned to have similar utility at low concentrations, and fall within the scope of the present invention. Incubation in the germination media is preferably carried out from about two to eight about weeks, and more preferably from about three to about four weeks.

The embryos are routinely monitored for germination. Embryos that have formed 2-3 leaves are generally transferred to a larger culture container and cultured further in the germination media. The germinated embryos, or plantlets, are maintained in culture at about 28° C. with an approximate 16/8 hour day/night cycle with about 30 μE to about 100 μE of light.

When plantlets have a total of four to six true leaves, the plantlets are transplanted to soil, grown in a growth chamber, and subsequently transferred to a greenhouse. In a preferred embodiment, MetroMix 350 (Hummerts Inc., St. Louis, Mo.) is used. A variety of soil mixtures are available and could be used in the practice of this invention. Plants are grown at about 28° C. with a 16/8 hour day/night cycle.

At this stage, the transgenic cotton plants may be analyzed for the presence of the DNA sequence introduced by the transformation. There are a variety of molecular and biochemical assays for detecting the DNA sequence or the encoded protein. These assays include western blotting, immunohistochemistry, ELISA, northern blotting, and Southern blotting. Once the presence of the nucleic acid sequence or the encoded protein is confirmed, these independent transgenic cotton lines may be further tested for agronomic efficacy under growth chamber, greenhouse, and field conditions.

The following examples are included to demonstrate preferred embodiments of the invention. It should be appreciated by those of skill in the art that the techniques disclosed in the examples represent techniques discovered by the inventors to function well in the practice of the invention, and thus constitute preferred modes for its practice. However, those of skill in the art should, in light of the present disclosure, appreciate that many changes and substitutions can be made in the specific embodiments that are disclosed and still obtain a like or similar result without departing from the spirit and scope of the invention.

EXAMPLES

Example 1

Preparation of Transgenic Callus

Media Preparation

Media employed in the transformation processes disclosed herein was prepared using standard methods known to those of skill in the art. Media formulations may be found in the cited references or with alterations or amendments as indicated. All media components and tissue culture materials are commercially available from a number of suppliers (for example, Sigma, St. Louis, Mo.).

Recombinant Nucleic Acid Vector Construction

Plasmid vectors were constructed using standard molecular biological techniques known to one of ordinary skill in the art. A number of Agrobacterium-mediated plant transformation vectors have been described. Briefly, the plant transformation vectors described herein comprise a nucleic acid sequence of interest; one or more T-DNA border sequences (promoting the transfer of nucleic acid sequences into the plant genome); replication elements; and a selectable marker. The features of the various recombinant nucleic acid vectors are summarized in Table 1. They are listed as follows: promoter, DNA sequence of interest, 3'-untranslated region, promoter, selectable marker, 3'-untranslated region.

The abbreviations in the table represent the following sequences. FMV is the 35S promoter from the Figwort Mosaic Virus (U.S. Pat. No. 5,378,619). The peFMV promoter is a modification of pFMV that introduces a duplicated region. The MAS promoter (DiRita and Gelvin, *Mol. Gen. Genet.*, 207:233-241,1987) is derived from a mannopine synthase gene. The pArabSSU1A promoter (Wong et al., *Plant Mol. Biol.*, 20:81-93, 1992) is derived from the RUBISCO small subunit promoter of Arabidopsis. The 35S promoter is derived from the 35S RNA of cauliflower mosaic virus (CaMV), and the e35S promoter is a modification of the 35S promoter containing a duplication of the −90 to −300 region. The petHSP70 leader is derived from the petunia heat shock protein (U.S. Pat. No. 5,362,865). The Act11 promoter is from the Arabidopsis actin 11 gene (Huang et al., *Plant Mol. Biol.*, 33:125-139,1997).

The nucleic acid sequences of interest include those conferring herbicide tolerance such as CP4, encoding an EPSP synthase that confers tolerance to glyphosate (U.S. Pat. No. 5,633,435); gox, which encodes a glyphosate oxidase (U.S. Pat. No. 5,463,175); B.t.k, which encodes a *Bacillus thuringiensis* insect control protein; ACC, which encodes an ACC deaminase (WO 92/12249); Chox, a sequence encoding a cholesterol oxidase (U.S. Pat. No. 5,763,245); and DSG, which encodes delta-9 desaturase.

The selectable marker sequences include the β-glucuronidase gene (GUS); nptII, which encodes a neomycin phosphotransferase and confers resistance to kanamycin; and a glyphosate tolerance gene such as CP4.

The 3' nontranslated regions include E9 3', derived from the 3' end of the pea rbcS E9 sequence (Coruzzi et al., *EMBO J.*, 3: 1671-1679, 1984); nos 3', the termination region of the sequence encoding a nopaline synthase protein; and 7S, which is the termination of the sequence encoding the soybean 7S seed storage protein.

TABLE 1

Recombinant Nucleic Acid Vectors.

| Plasmids | Sequence Elements |
|---|---|
| pMON10079 | pFMV, EPSP synthase, E93'; p35S, nptII, nos3' |
| pMON10565 | pMAS, B.t.k., 7S3'; p35S, nptII, nos3' |
| pMON10155 | pFMV, CP4, E93' |
| pMON10126 | pFMV, petHSP70L, ACC, E93'; pFMV, β-glucuronidase, nos3' |
| pMON10517 | pFMV, B.t.k., E93'; p35S, nptII, nos3' |
| pMON10837 | pArab-SSU1A, Arab-SSU1A transit peptide, B.t.k., E93'; 35S, nptII, nos3' |
| pMON17136 | pFMV, GOX, nos3'; pFMV, CP4, E93', p35S, nptII, nos3' |
| pMON20912 | pFMV, petHSP70L, Chox, E93', p35S, nptII, nos3' |
| pMON21446 | peFMV, petHSP70L, B.t.k., E93'; 35S, nptII, nos3' |
| pMON20956 | pe35S, Arab SSU1A transit peptide, B.t.k., E93', 35S, nptII, nos3' |
| pMON42611 | pe35S, ESG, nos3'; p35S, nptII, nos3' |
| pMON45325 | pAct11, CP4, E93'; peFMV, CP4, E93' |

Preparation of Agorobacterium

Agrobacterium strain C58 was streaked from a glycerol stock onto a LB plate (10 g/L sodium chloride, 5 g/L yeast extract, 10 g/L bacto-tryptone solidified with 15 g/L agar) containing the following selective antibiotics per liter: spectinomycin (1 mL of a 50 mg/mL stock), streptomycin (1 mL of a 50 mg/mL stock), chloramphenicol (1 mL of a 25 mg/mL stock), and kanamycin (1 mL of a 50 mg/mL stock). The plate was incubated at about 28° C. for about 3 days. A single colony was used to inoculate a liquid culture of LB containing selective antibiotics described above.

Seed Sterilization, Germination, and Tissue Preparation

Cotton seeds (Coker 312) were surfaced sterilized. The seeds were removed from 4° C. storage and approximately 80 grams were added to a one-liter flask. About 2 teaspoons of a detergent such as Sparkleen detergent (Fisher Scientific, St. Louis, Mo.) were added to about 700-800 mL of water. The flask was capped and the seeds shaken and allowed to soak for 10 minutes. The flask was occasionally swirled during the soaking process to wash the seeds thoroughly.

The detergent solution was poured off the seeds, and the seeds were washed with 300-400 mL of a solution of 30-50% bleach. The seeds were soaked for 30 minutes and rinsed several times. Seeds were germinated in the dark or lightlimiting conditions on ½ MS media in a tall tissue culture vessel such as a PHYTATRAY (PHYTATRAY is a registered trademark of Sigma Chemical Co., St. Louis, Mo.) for about five to ten days. The hypocotyl segments were removed from the dark or limited-light grown seedlings and sectioned into small pieces from about 3-10 mm prior to inoculation.

Inoculation and Co-Culture

Liquid overnight cultures of Agrobacterium harboring the nucleic acid vector of interest were prepared. Hypocotyls obtained from the germinated seeds were cut into pieces and inoculated with the Agrobacterium suspension. The inoculated tissue was co-cultured on 1/10 MS media for two to four days at room temperature.

Selection of Transformed Cells

After co-culture, the tissue was transferred to selective media. The selective media was an MS-based media that contained the following components per liter: 4.3 g MS salts with $B_5$ vitamins, 0.1 mL 2,4-D (1 mg/mL), 0.5 mL kinetin (1 mg/mL), 30 g glucose, pH 5.8, 0.25% (w/v) GELRITE, 2 mL carbenicillin (250 mg/mL), 1 mL cefotaxime (100 mg/mL) and a selective agent, either kanamycin (15-150 mg/L) or glyphosate (0.5-2.5 mM). The cultures were incubated at 28° C. with a 16/8 day/night cycle.

Approximately four weeks after the initial transfer to selection media, the hypocotyls were transferred to fresh selection media, and the tissue was incubated at 28° C. with a 16/8 day/night cycle. Successfully transformed tissue survived in the selection culture and formed transgenic calli.

Example 2

Use of Dark or Limited Lighting Conditions During Embryo Induction

The transgenic calli were removed from the hypocotyls and transferred to a culture containing hormone-free media comprising the following components per liter: 4.4 g MS salts with $B_5$ vitamins; 30 g glucose, pH 5.8; an antioxidant, such as ascorbic acid (10-100 mg); an ethylene inhibitor, such as aminoethoxyvinylglycine at approximately 5 µM; GELRITE or PHYTAGEL (2-3 g); and selective agents as described above. This culture was maintained at 28° C. under conditions of dark or limited lighting. The dark or limited lighting conditions were accomplished using a black bag, a covering of aluminum foil, or by incubating in a dark growth chamber. Alternatively, the transgenic calli may be incubated under green light. The incubation is continued for about eight to ten weeks.

The positive effect of various lighting conditions on the induction of embryogenesis in transgenic callus was demonstrated in several separate experiments using Coker 312 (Tables 2 and 3). Cotton calli, transformed with four different recombinant nucleic acid vectors, were tested in light (50-100 µE, 16-hour photoperiod) versus dark (black bags or dark growth room). In each experiment, at least 200 calli were tested.

The results indicated that a substantial increase in the frequency of embryogenic calli is obtained by maintaining the culture plates under dark or limited lighting conditions. In Table 2, maintaining the cultures in the dark for embryo induction increased the frequency of embryogenic callus formation from two- to fivefold. The frequency of embryogenic calli formation was also significantly increased when the cultures were maintained in a dark growth chamber (Table 3).

TABLE 2

Effect of Dark (Black Bag) on Induction of Embryogenesis.

| Treatment | Frequency of Embryogenic Calli |
|---|---|
| Experiment 1: pMON20912 vector | |
| light | 3% |
| black bags | 16% |
| Experiment 2: pMON10126 vector | |
| light | 14% |
| black bags | 44% |
| Experiment 3: pMON20912 vector | |
| light | 10% |
| black bags | 21% |
| Experiment 4: pMON10565 vector | |
| light | 12% |
| black bags | 32% |

TABLE 3

Effect of Dark (Growth Room) on Induction of Embryogenesis*.

| Treatment | Calli Tested | Embryogenic Calli Formed | Frequency |
|---|---|---|---|
| light | 281 | 82 | 29% |
| dark (growth room) | 280 | 234 | 84% |

*pMON21446 vector

Example 3

Use of Antioxidants During Embryo Induction

The positive influence of antioxidants on the induction of embryogenesis in Coker 312 was also demonstrated (Table 4). In two independent experiments, ascorbic acid was shown to increase the frequency of embryogenesis. The results demonstrate that supplementing the media with 10-100 mg/L of an antioxidant significantly stimulates induction of cotton callus embryogenesis.

TABLE 4

Effect of Ascorbic Acid on the Induction of Embryogenesis.

| Recombinant Nucleic Acid Vector | Ascorbic Acid Concentration (mg/mL) | % Embryogenic Calli Transfer 1 | % Embryogenic Calli Transfer 2 | Total Frequency of Embryogenesis |
|---|---|---|---|---|
| pMON20956 | 0 | 0% | 26% | 26% |
| pMON20956 | 10 | 2% | 33% | 35% |
| pMON20956 | 100 | 3% | 31% | 34% |
| pMON10155 | 0 | 9% | 9% | 28% |
| pMON10155 | 10 | 18% | 16% | 34% |

Example 4

Use of Ethylene Inhibitors During Embryo Induction

In two separate experiments, the ethylene inhibitors AVG (aminoethoxy-vinylglycine), DNP (2,4-dinitrophenol), and salicylic acid were tested to determine their influence on the induction of embryogenic cotton calli. The results demonstrate that ethylene inhibitors have a positive impact on the frequency of embryo formation. Of the inhibitors tested, AVG increased the frequency of embryogenic callus formation most significantly relative to the non-AVG treated controls (Table 5).

TABLE 5

Effect of Ethylene Inhibitors on Embryogenic Callus Formation.

| Treatment | Calli Tested | Embryogenic Calli Formed | Frequency of Formation |
|---|---|---|---|
| Expt 1 pMON10517 | | | |
| control | 40 | 13 | 33% |
| 5 μM AVG | 40 | 20 | 50% |
| 1 μM DNP | 40 | 17 | 43% |
| 50 μM salicylic acid | 40 | 12 | 30% |
| Expt 2 pMON10079 | | | |
| control | 40 | 16 | 40% |
| 5 μM AVG | 40 | 21 | 53% |
| 1 μM DNP | 40 | 16 | 40% |
| 50 μM salicylic acid | 40 | 17 | 43% |

Example 5

Use of an Amino Acid Supplement During Embryo Maturation

The preparation of Agrobacterium, seed sterilization, seed germination, inoculation, co-culture, and selection were performed as described in Example 1. Induction of embryogenesis in the transgenic calli was completed as described in Example 2. From eight to ten weeks the cultures were maintained in the dark on media supplemented with AVG and ascorbic acid as described in Example 2. The cultures were routinely checked for the production of embryogenic calli. Any embryogenic tissue formed was removed from non-embryogenic tissues and transferred to a culture containing a MS-based maturation media comprising 4.4 g/L MS salts with $B_5$ vitamins; 1.9 g/L $KNO_3$; 30 g/L glucose, pH 5.8; 0.1 g/L casein hydrolysate; and 2 g/L GELRITE. A piece of sterile filter paper was added to the top of the media prior to the addition of the tissue. The tissue was placed in a lighted incubator/warm at 28° C. with 16/8 day/night cycle and routinely checked for the presence of actively growing embryos.

The effect of supplementing the maturation media with casein hydrolysate was tested. In two separate experiments, results demonstrated that the addition of 100 mg/L casein hydrolysate substantially increased the number of mature embryogenic callus lines observed relative to controls lacking the casein hydrolysate supplement (Table 6).

TABLE 6

Effect of Casein Hydrolysate on Embryogenesis.

| Construct | Initial # of Lines | Treatment | # Embryogenic Lines (%) |
|---|---|---|---|
| pMON17136 | 100 | −casein | 27 (27) |
| pMON17136 | 100 | +casein | 48 (48) |
| pMON10837 | 86 | −casein | 31 (36) |
| pMON10837 | 86 | +casein | 42 (49) |

Example 6

Use of a Support Matrix During Embryo Maturation

The effect of a support matrix such as filter paper was also tested and found to have a positive influence on cotton embryo maturation. Placing filter paper on the culture media during embryo maturation improved the frequency that cultures produced mature embryos, both for new embryogenic lines and recalcitrant embryogenic lines. The results comparing two different brands of filter paper including Whatman (Fisher Scientific Corp., Pittsburgh, Pa.) and Baxter (Fisher Scientific Corp., Pittsburgh, Pa.) relative to a control without filter paper are shown in Tables 7 and 8.

TABLE 7

Effect of Support Matrix on Embryo Maturation - pMON20912 construct.

| Treatment | # Plates | # Lines Producing Embryos | Frequency of Lines Producing Embryos |
|---|---|---|---|
| Transfer 1 | | | |
| Control | 123 | 4 | 3% |
| Baxter | 10 | 0 | 0% |
| Whatman | 10 | 0 | 0% |
| Transfer 2 | | | |
| Control | 117 | 16 | 14% |
| Baxter | 10 | 2 | 20% |
| Whatman | 9 | 4 | 44% |
| Transfer 3 | | | |
| Control | 117 | 20 | 17% |
| Baxter | 10 | 2 | 20% |
| Whatman | 9 | 3 | 33% |
| Transfer 4 | | | |
| Control | 117 | 18 | 15% |
| Baxter | 10 | 2 | 20% |
| Whatman | 9 | 5 | 55% |
| Transfer 5 | | | |
| Control | 117 | 6 | 5% |
| Baxter | 10 | 3 | 30% |
| Whatman | 9 | 3 | 33% |

TABLE 8

Effect of Support Matrix on Embryo Maturation - pMON10565 construct.

| Treatment | # Plates | # Lines Producing Embryos | Frequency of Lines Producing Embryos |
|---|---|---|---|
| Transfer 1 | | | |
| Control | 211 | 10 | 5% |
| Baxter | 19 | 10 | 53% |
| Whatman | 15 | 6 | 40% |
| Transfer 2 | | | |
| Control | 211 | 36 | 17% |
| Baxter | 18 | 12 | 67% |
| Whatman | 15 | 10 | 67% |
| Transfer 4 | | | |
| Control | 209 | 20 | 10% |
| Baxter | 18 | 7 | 39% |
| Whatman | 14 | 10 | 71% |
| Transfer 5 | | | |
| Control | 204 | 23 | 11% |
| Baxter | 18 | 11 | 61% |
| Whatman | 12 | 6 | 50% |

TABLE 8-continued

Effect of Support Matrix on Embryo Maturation - pMON10565 construct.

| Treatment | # Plates | # Lines Producing Embryos | Frequency of Lines Producing Embryos |
|---|---|---|---|
| Transfer 6 | | | |
| Control | 204 | 58 | 28% |
| Baxter | 18 | 13 | 72% |
| Whatman | 12 | 7 | 58% |
| Transfer 7 | | | |
| Control | 204 | 20 | 10% |
| Baxter | 18 | 10 | 55% |
| Whatman | 12 | 9 | 75% |

Example 7

Use of Dark Growth Conditions and Parafilm during Embryo Maturation

For the light treatment tissue was incubated in a 16/8 day/night cycle at 28° C. in an incubator/warm room. For the dark treatment, tissue was incubated in continuous dark at 28° C. in an incubator/warm room. The plates containing the tissue were either sealed in PARAFILM M (American National Can, Chicago, Ill.) or incubated without being sealed.

The effect of dark growth conditions and PARAFILM were tested and compared to lighted conditions without PARAFILM treatment. Dark growth conditions combined with sealing the plates with PARAFILM increased the frequency of embryo maturation and germination (Table 9).

TABLE 9

Effect of Dark Growth Conditions and PARAFILM on Embryo Maturation and Germination (pMON42611)

| Lighting | Wrap treatment | # Lines tested | # Lines with plantlets | Frequency of plantlet formation per line |
|---|---|---|---|---|
| light | unwrapped | 30 | 11 | 37% |
| light | PARAFILM | 30 | 15 | 50% |
| dark | unwrapped | 30 | 7 | 23% |
| dark | PARAFILM | 30 | 21 | 70% |

Example 8

Use of Low Concentration of Carbohydrate During Embryo Germination

The preparation of Agrobacterium, seed sterilization, seed germination, inoculation, co-culture, and selection were performed as described in Example 1. Embryos were induced as outlined in Examples 2, 3, and 4. After eight weeks, the embryogenic tissue that formed was transferred to an embryo maturation media as described in Examples 5 and 6. Cultures were monitored for the presence of actively growing embryos.

About every four weeks, actively growing tissue and small embryos were removed and placed on fresh maturation media. The embryos were spaced on the culture plates with adequate room for growth. The tissue was returned to the warm room and incubated under the same growth conditions.

Embryos larger than about 5 mm were transferred to a germination media (Stewart and Hsu, *Planta* 137:113-117, 1997) with various carbohydrate concentrations and 0.25 g/L GELRITE. The embryos are incubated at 28° C. in a lighted incubator with a 16/8 day/night cycle.

Various concentrations of glucose and sucrose in the germination media were tested. The germination media comprised sucrose or glucose at concentrations ranging from about 0%-2% (w/v). The results demonstrated that using germination media containing glucose or sucrose concentrations ranging from about 0% to 0.5% (w/v) significantly increased the frequency of embryo germination and plantlet formation (Table 10).

TABLE 10

Effect of Varying the Carbohydrate Concentration on Embryo Germination.

| Germination Media | # Plantlets with Expanded Leaves | Total # Embryos | Transformation Frequency |
|---|---|---|---|
| no carbohydrate | 9 | 19 | 47% |
| 0.1% sucrose | 7 | 15 | 47% |
| 0.5% sucrose | 10 | 23 | 43% |
| 1% sucrose | 6 | 22 | 27% |
| 2% sucrose | 5 | 18 | 28% |
| 0.1% glucose | 15 | 23 | 65% |
| 0.5% glucose | 19 | 26 | 73% |
| 1% glucose | 4 | 21 | 19% |
| 2% glucose | 0 | 21 | 0% |

After embryos had germinated and developed about 3-4 leaves, the tissues were transferred to a larger container containing the same germination media. Once the plants developed 4-6 total leaves, they were transferred to pots containing Metro-Mix 350 and slowly hardened off.

Example 9

Comparison of Protocols

Plantlets were generated using both the improved protocol, designated protocol 2, and the protocol prior to improvement, designated protocol 1. Table 11 compares efficiencies of the two protocols set up simultaneously using the same vector construct. Protocol 2 consisted of the procedure described in Example 1 for media preparation, recombinant nucleic acid vector construction, preparation of Agrobacterium, seed sterilization, germination and tissue preparation, inoculation and co-culture, and selection of transformed cells, Example 2 (incubation in dark growth chamber), Example 3 (100 mg/L ascorbic acid), Example 5 (0.1 g/L casein hydrolysate), Example 6 (Whatman filter paper) and Example 8 (0.5% glucose).

Protocol 1 consisted of the procedure described in Example 1 for media preparation, recombinant nucleic acid vector construction, preparation of Agrobacterium, seed sterilization, germination and tissue preparation, inoculation and co-culture, and selection of transformed cells. For the embryo induction procedure, transgenic calli were removed from the hypocotyls and transferred to a culture containing hormone-free media comprising the following components per liter: 4.4 g MS salts with $B_5$ vitamins; 30 g glucose, pH 5.8; GELRITE or PHYTAGEL (2-3 g); and selective agents as described above. This culture was maintained at 28° C. under a 16/8 day/night in an incubator/warm room. The incubation was continued for about eight to ten weeks. Embryo maturation procedure consisted of routinely checking the cultures for the production of embryogenic calli. Any embryogenic tissue formed was removed from non-embryogenic tissues and transferred to a culture containing a MS-based maturation media comprising 4.4 g/L MS salts with B$_5$ vitamins; 1.9 g/L KNO$_3$; 30 g/L glucose, pH 5.8; and 2 g/L GELRITE. The tissue was placed in a lighted incubator/warm at 28° C. with 16/8 day/night cycle and routinely checked for the presence of actively growing embryos. About every four weeks, actively growing tissue and small embryos were removed and placed on fresh media maturation media. The embryos were spaced on the culture plates with adequate room for growth. The tissue was returned to the warm room and incubated under the same growth conditions. Embryos larger than about 5 mm were transferred to a germination media (Stewart and Hsu, *Planta* 137:113-117, 1997) with 0.25 g/L GELRITE. The embryos were incubated at 28° C. in a lighted incubator with a 16/8 day/night cycle.

TABLE 11

Comparison of Protocol 1 to Protocol 2 using pMON45325

Induction of embryogenesis

| Treatment | # Calli | # Embryogenic calli | Frequency |
|---|---|---|---|
| protocol 1 | 1004 | 122 | 12% |
| protocol 2 | 875 | 398 | 45% |

Maturation of embryogenic calli

| Treatment | # Embryogenic calli | # Events | Frequency |
|---|---|---|---|
| protocol 1 | 122 | 17 | 14% |
| protocol 2 | 398 | 226 | 57% |

Overall efficiency

| Treatment | # Explants | # Plantlets | Frequency |
|---|---|---|---|
| protocol 1 | 500 | 2 | 0.4% |
| protocol 2 | 500 | 32 | 6.0% |

All of the compositions and/or methods disclosed and claimed herein can be made and executed without undue experimentation by one of skill in the art in light of the present disclosure. Although the compositions and methods of this invention have been described in terms of preferred embodiments, it will be apparent to those of skill in the art that variations may be applied to the compositions, methods, and steps (or sequence of steps) described herein without departing from the concept and scope of the invention. Furthermore, it will be particularly apparent that certain agents that are both chemically and physiologically related may be substituted for the agents described herein while achieving equivalent results. All such similar substitutes and modifications apparent to those skilled in the art are deemed to be within the scope and concept of the invention.

The invention claimed is:

1. A method of culturing transformed regenerable non-embryogenic cotton callus tissue comprising culturing said cotton callus tissue in a medium containing an antioxidant and an ethylene inhibitor under dark lighting conditions of 0 μEinsteins m$^{-2}$sec$^{-1}$ to induce a regenerable embryogenic callus.

2. The method of claim 1, wherein the ethylene inhibitor is aminoethoxyvinylglycine.

3. The method of claim 1, wherein: the antioxidant is ascorbic acid; and the ethylene inhibitor is aminoethoxyvinylglycine.

4. The method of claim 1, wherein the regenerable non-embryogenic cotton callus tissue is derived from callus, hypocotyl, cotyledon, root, petiole, anther, or leaf.

5. A method of culturing transgenic cotton embryos comprising:
culturing transformed regenerable non-embryogenic cotton callus tissue in a medium containing an antioxidant and an ethylene inhibitor under dark lighting conditions of 0 Einsteins m$^{-2}$sec$^{-1}$ to produce transgenic embryogenic cotton tissue; and culturing the transgenic embryogenic cotton tissue on an embryo maturation medium with a support matrix.

6. The method of claim 5, wherein the ethylene inhibitor is aminoethoxyvinylglycine.

7. The method of claim 5, wherein: the antioxidant is ascorbic acid; and the ethylene inhibitor is aminoethoxyvinylglycine.

8. The method of claim 5, wherein the support matrix is filter paper.

9. A method of culturing regenerable non-embryogenic cotton callus tissue comprising culturing said cotton callus tissue in a medium containing an antioxidant and an ethylene inhibitor under dark lighting conditions of 0 μEinsteins$^{-2}$sec$^{-1}$ to produce embryogenic cotton tissue; and culturing the embryogenic cotton tissue in a medium containing a support matrix and an amino acid hydrolysate supplement.

10. The method of claim 9, wherein the concentration of the amino acid supplement in the medium is between about 10 mg/L and about 500 mg/L.

11. The method of claim 10, wherein the concentration of the amino acid supplement in the medium is between about 50 mg/L and about 150 mg/L.

12. The method of claim 9, wherein the ethylene inhibitor is aminoethoxyvinylglycine.

13. The method of claim 9, wherein the antioxidant is ascorbic acid; and the ethylene inhibitor is aminoethoxyvinylglycine.

14. The method of claim 9, wherein the support matrix is filter paper.

15. A method of culturing regenerable non-embryogenic cotton callus tissue comprising culturing said cotton callus tissue in a medium containing an antioxidant and an ethylene inhibitor under dark lighting conditions of 0 μEinsteins$^-$$_2$sec$^{-1}$ to produce embryogenic cotton tissue; and culturing the embryogenic cotton tissue in a medium containing a support matrix and an amino acid hydrolysate supplement under dark lighting conditions, limited lighting conditions or under green light and wrapped with a sealing material.

16. The method of claim 15, wherein the ethylene inhibitor is aminoethoxyvinylglycine.

17. The method of claim 15, wherein the antioxidant is ascorbic acid; and the ethylene inhibitor is aminoethoxyvinylglycine.

18. The method of claim 15, wherein the support matrix is filter paper.

* * * * *

UNITED STATES PATENT AND TRADEMARK OFFICE
CERTIFICATE OF CORRECTION

| | | |
|---|---|---|
| PATENT NO. | : 7,790,460 B2 | Page 1 of 1 |
| APPLICATION NO. | : 10/692762 | |
| DATED | : September 7, 2010 | |
| INVENTOR(S) | : Armstrong et al. | |

It is certified that error appears in the above-identified patent and that said Letters Patent is hereby corrected as shown below:

Title page, item 60, insert --Provisional application No. 60/112,770, filed on Dec. 18, 1998, now abandoned.--.

Title page, item 62, insert --Continuation of application No. 09/466,629, filed on Dec. 17, 1999.--.

In claim 9, column 22, line 27, delete "$\mu Einsteins^{-2}sec^{-1}$" and insert --$\mu Einsteins\ m^{-2}sec^{-1}$--.

In claim 15, column 22, line 47, delete "$\mu Einsteins^{-2}sec^{-1}$" and insert --$\mu Einsteins\ m^{-2}sec^{-1}$--.

Signed and Sealed this
Twelfth Day of July, 2011

David J. Kappos
*Director of the United States Patent and Trademark Office*